US012599296B2

(12) United States Patent
Niwa

(10) Patent No.: US 12,599,296 B2
(45) Date of Patent: Apr. 14, 2026

(54) MEDICAL LIGHT SOURCE DEVICE AND MEDICAL OBSERVATION SYSTEM

(71) Applicant: Sony Olympus Medical Solutions Inc., Tokyo (JP)

(72) Inventor: Yoshiaki Niwa, Tokyo (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 517 days.

(21) Appl. No.: 18/172,338

(22) Filed: Feb. 22, 2023

(65) Prior Publication Data

US 2023/0284890 A1    Sep. 14, 2023

(30) Foreign Application Priority Data

Mar. 9, 2022    (JP) ................................. 2022-036581

(51) Int. Cl.
    *A61B 1/06*       (2006.01)
    *A61B 1/00*       (2006.01)
    *G01M 11/00*    (2006.01)

(52) U.S. Cl.
    CPC ........ *A61B 1/0655* (2022.02); *A61B 1/00055* (2013.01); *A61B 1/063* (2013.01); *A61B 1/0638* (2013.01); *G01M 11/3109* (2013.01)

(58) Field of Classification Search
    CPC ... A61B 1/0655; A61B 1/00055; A61B 1/063; A61B 1/0638; A61B 1/00006; A61B 1/0669; A61B 1/01; G01M 11/3109; G02B 23/2469; G02B 23/2484; G02B 23/26
    See application file for complete search history.

(56) References Cited

U.S. PATENT DOCUMENTS

| | | | | |
|---|---|---|---|---|
| 5,263,109 A | * | 11/1993 | Abe ..................... | G02B 6/2821 250/227.12 |
| 5,452,071 A | * | 9/1995 | Takeuchi ........... | G01M 11/3109 356/73.1 |
| 5,647,368 A | * | 7/1997 | Zeng ................... | A61B 5/4255 600/476 |
| 5,777,727 A | * | 7/1998 | Sato ........................ | G01J 11/00 356/73.1 |
| 7,018,331 B2 | * | 3/2006 | Chang ................... | A61B 1/045 385/101 |
| 10,588,488 B2 | * | 3/2020 | Suzuki .............. | A61B 1/00156 |
| 2005/0027166 A1 | * | 2/2005 | Matsumoto .......... | A61B 1/0655 977/852 |
| 2005/0279354 A1 | * | 12/2005 | Deutsch ............ | A61M 16/0463 128/200.24 |

(Continued)

FOREIGN PATENT DOCUMENTS

WO     WO-2021006438 A1    1/2021

*Primary Examiner* — Anh Tuan T Nguyen
*Assistant Examiner* — Jae Woo
(74) *Attorney, Agent, or Firm* — XSENSUS LLP

(57) ABSTRACT

A medical light source device includes: a first light source configured to emit laser light; a second light source configured to emit measurement light for measuring a connection state between a light guide configured to guide the laser light and an emission optical system configured to irradiate a subject with the laser light through the light guide to the light guide; and a control unit configured to control output of the laser light in the first light source based on return light of the measurement light emitted from the second light source.

20 Claims, 8 Drawing Sheets

(56) References Cited

U.S. PATENT DOCUMENTS

| | | | |
|---|---|---|---|
| 2014/0111795 A1* | 4/2014 | Barnhart | G01M 11/3145 |
| | | | 356/73.1 |
| 2017/0095137 A1* | 4/2017 | Kinouchi | A61B 1/00055 |
| 2018/0008124 A1* | 1/2018 | Fujimoto | A61B 1/00059 |
| 2020/0072703 A1* | 3/2020 | Roux | G01M 11/3145 |
| 2020/0240872 A1* | 7/2020 | Murakami | G01M 11/3145 |
| 2021/0135752 A1* | 5/2021 | L'Heureux | H04B 10/035 |
| 2021/0386279 A1* | 12/2021 | Levesque | H04N 23/555 |
| 2022/0299401 A1* | 9/2022 | Honda | G01M 11/0242 |
| 2023/0324235 A1* | 10/2023 | Champavere | G01D 5/35361 |
| | | | 376/161 |
| 2023/0400381 A1* | 12/2023 | Takasu | G01M 11/3109 |
| 2024/0337559 A1* | 10/2024 | Andresen | G01M 11/3154 |

* cited by examiner

MEDICAL LIGHT SOURCE DEVICE AND MEDICAL OBSERVATION SYSTEM

This application claims priority from Japanese Application No. 2022-036581, filed on Mar. 9, 2022, the contents of which are incorporated by reference herein in its entirety.

BACKGROUND

The present disclosure relates to a medical light source device and a medical observation system.

In recent years, in a medical observation system for observing a subject, laser light having a narrow band and high coherence may be used as light for observing the subject.

Such a medical observation system includes a rigid endoscope, a light guide, and a medical light source device described below, for example.

The medical light source device emits laser light.

The light guide connects the rigid endoscope and the medical light source device and guides the laser light emitted from the medical light source device to the rigid endoscope.

The rigid endoscope is inserted into the subject and irradiates from its distal end the inside of the subject with the laser light guided by the light guide. The rigid endoscope captures a subject image inside the subject.

The light guide may be easily detached from the rigid endoscope without using a tool. That is, when the light guide is detached from the rigid endoscope, there is a possibility that the user is irradiated with the laser light emitted from an emission end of the light guide. To ensure safety, it is necessary to design laser light emitted from the emission end of the light guide to satisfy the requirement defined in the laser standard indicating the "Safety of Laser Products". In such a design, the light amount of laser light emitted from the emission end of the light guide is limited by the laser standard, and as a result, it is difficult to secure the light amount of the laser light emitted from the distal end of the rigid endoscope.

A medical observation system that emits laser light from a medical light source device only when connection between a light guide and a rigid endoscope is detected has been proposed (see U.S. Pat. No. 7,018,331, for example).

In the medical observation system described in U.S. Pat. No. 7,018,331, connection between the light guide and the rigid endoscope is detected by using a detection attachment that incorporates an object to be detected such as a radio frequency identifier (RFID) tag.

Specifically, the light guide is provided with a detector that detects the above-described object to be detected. Connecting the detection attachment to the rigid endoscope and then connecting the light guide to the detection attachment causes the detector provided in the light guide to detect the object to be detected built in the detection attachment. This causes connection between the light guide and the rigid endoscope to be detected.

With the configuration in which the medical light source device emits laser light only when the light guide and the rigid endoscope are connected, the laser light is not emitted from the emission end of the light guide when the light guide is detached from the rigid endoscope. That is, in such a configuration, the laser light emitted from the distal end of the rigid endoscope is designed to satisfy the requirement defined in the laser standard indicating the "Safety of Laser Products". Then, with such a design, the light amount of laser light emitted from the emission end of the light guide may be set to be high without being limited by the laser standard, and as a result, it is possible to secure the light amount of the laser light emitted from the distal end of the rigid endoscope.

SUMMARY

However, the medical observation system described in U.S. Pat. No. 7,018,331 has the following problem when the connection procedure of the detection attachment is mistaken.

That is, when the detection attachment is connected to the light guide first, connection between the light guide and the rigid endoscope is detected although the light guide and the rigid endoscope are not connected. This causes laser light to be emitted from the emission end of the light guide without connection between the light guide and the rigid endoscope. That is, safety may not be ensured.

Thus, there is a demand for a technique capable of securing the light amount of laser light emitted to a subject while securing safety.

According to one aspect of the present disclosure, there is provided a medical light source device including: a first light source configured to emit laser light; a second light source configured to emit measurement light for measuring a connection state between a light guide configured to guide the laser light and an emission optical system configured to irradiate a subject with the laser light through the light guide to the light guide; and a control unit configured to control output of the laser light in the first light source based on return light of the measurement light emitted from the second light source.

DETAILED DESCRIPTION

Figure 1:
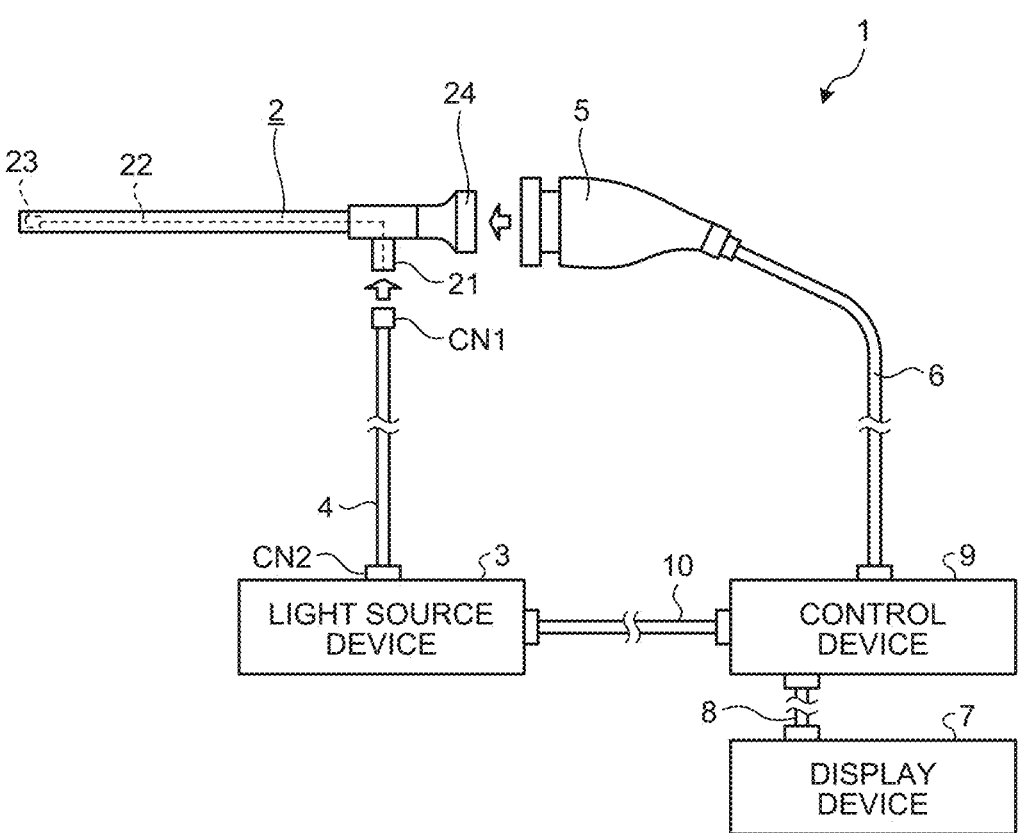
FIG. 1 is a diagram illustrating a medical observation system according to an embodiment.

Hereinafter, modes for carrying out the present disclosure (hereinafter referred to as "embodiments") will be described with reference to the drawings. The present disclosure is not limited by the embodiments described below. In the description of the drawings, the same portions are denoted by the same reference numerals.

FIG. 1 is a diagram illustrating a medical observation system 1 according to an embodiment.

The medical observation system 1 is a system that is used in the medical field and observes a subject (inside of a living body). As illustrated in FIG. 1, the medical observation system 1 includes an insertion unit 2, a light source device 3, a light guide 4, a camera head 5, a first transmission cable 6, a display device 7, a second transmission cable 8, a control device 9, and a third transmission cable 10.

The insertion unit 2 corresponds to an emission optical system according to the present disclosure. In the present embodiment, the insertion unit 2 is composed of a rigid endoscope. That is, the insertion unit 2 has an elongated shape that is entirely rigid or partially soft and partially rigid, and is inserted into the living body.

In the insertion unit 2, an optical system (not illustrated) configured by using one or a plurality of lenses to collect a subject image is provided.

As illustrated in FIG. 1, the insertion unit 2 is provided with a fiber connection unit 21 to which a connector CN1 of the light guide 4 is detachably connected. In the insertion unit 2, an optical fiber 22 and a concave lens 23 are provided.

The optical fiber 22 extends from the fiber connection unit 21 to the distal end side of the insertion unit 2 and guides light incident through the fiber connection unit 21 to the distal end side of the insertion unit 2.

The concave lens 23 is provided at the distal end of the insertion unit 2 and irradiates the living body with the light guided by the optical fiber 22 from the distal end of the insertion unit 2.

The light source device 3 corresponds to a medical light source device according to the present disclosure. The light source device 3 is connected to a connector CN2 of the light guide 4 and supplies light (normal light such as white light or excitation light (laser light)) designated by the control device 9 to the incident end of the light guide 4 under the control of the control device 9. In the present embodiment, the light source device 3 is configured separately from the control device 9, but the light source device 3 is not limited to this configuration. The light source device 3 may be provided in the control device 9.

A detailed configuration of the light source device 3 will be described in "Configuration of light source device" described later.

In the light guide 4, the connector CN1 on the emission end side is detachably connected to the fiber connection unit 21, and the connector CN2 on the incident end side is detachably connected to the connector CN3 (see FIG. 2) of the light source device 3. An optical fiber (not illustrated) is provided inside the light guide 4, and light (normal light such as white light or excitation light (laser light)) supplied from the light source device 3 is supplied to the optical fiber 22 through the fiber connection unit 21. The light supplied to the optical fiber 22 is emitted into the living body through the concave lens 23. Normal light or excitation light (laser light) reflected in the living body and fluorescence emitted from a fluorescent substance in the living body when the fluorescent substance is excited by the excitation light are collected by the optical system in the insertion unit 2.

The camera head 5 is detachably connected to an eyepiece unit 24 of the insertion unit 2. Under the control of the control device 9, the camera head 5 captures the subject image collected by the insertion unit 2 and generates an image signal (hereinafter referred to as "captured image").

One end of the first transmission cable 6 is detachably connected to the control device 9, and the other end is detachably connected to the camera head 5. The first transmission cable 6 transmits the captured image and the like output from the camera head 5 to the control device 9 and transmits a control signal, a synchronization signal, a clock, power, and the like output from the control device 9 to the camera head 5.

In the transmission of the captured image and the like from the camera head 5 to the control device 9 through the first transmission cable 6, the captured image and the like may be transmitted as an optical signal or may be transmitted as an electrical signal. The same applies to the transmission of a control signal, a synchronization signal, and a clock from the control device 9 to the camera head 5 through the first transmission cable 6.

The display device 7 is composed of a display using liquid crystal, organic electro luminescence (EL), or the like, and displays an image based on a video signal from the control device 9 under the control of the control device 9.

One end of the second transmission cable 8 is detachably connected to the display device 7, and the other end is detachably connected to the control device 9. The second transmission cable 8 transmits the video signal processed by the control device 9 to the display device 7.

The control device 9 is composed of a central processing unit (CPU), a field-programmable gate array (FPGA), and the like, and it integrally controls operations of the light source device 3, the camera head 5, and the display device 7. For example, the control device 9 outputs a control signal to the light source device 3 according to an observation mode such as a normal observation mode or a fluorescence observation mode, and causes the light source device 3 to emit light (normal light such as white light or excitation light (laser light)) corresponding to the observation mode. Further, the control device 9 executes various types of image processing on the captured image output from the camera head 5 and generates a video signal for displaying the captured image. Then, the control device 9 outputs the video signal to the display device 7 through the second transmission cable 8 to cause the display device 7 to display the captured image based on the video signal.

One end of the third transmission cable 10 is detachably connected to the light source device 3, and the other end is detachably connected to the control device 9. The third transmission cable 10 transmits the control signal from the control device 9 to the light source device 3.

Figure 2:
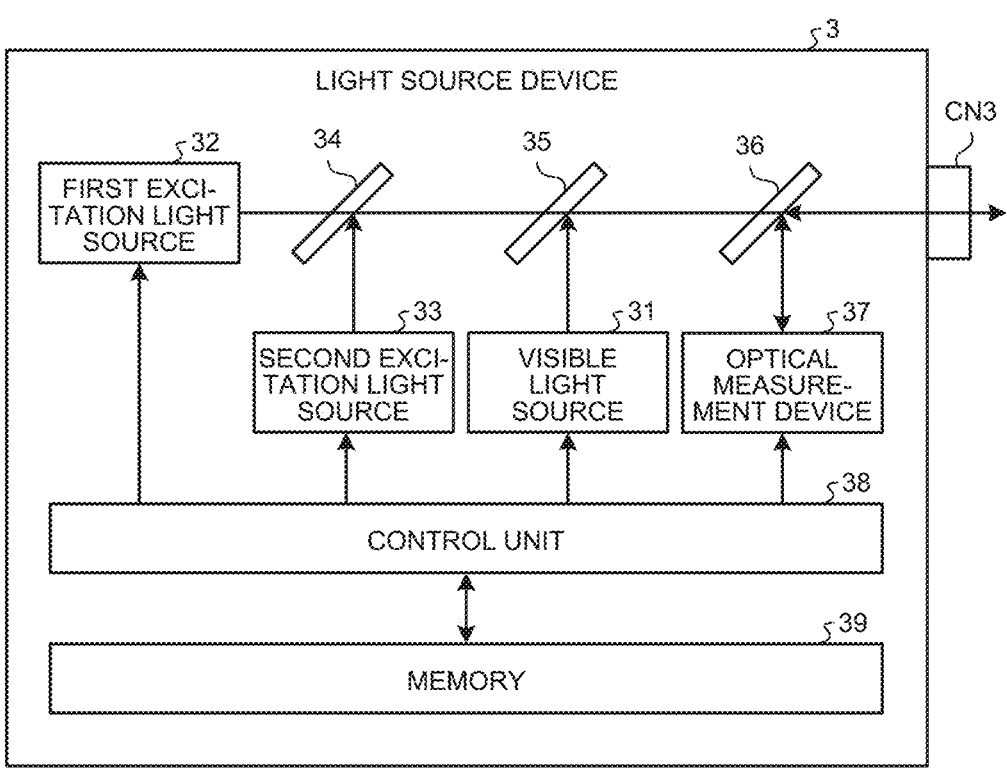
FIG. 2 is a block diagram illustrating a configuration of a light source device.

FIG. 2 is a block diagram illustrating a configuration of the light source device 3.

Next, a configuration of the light source device 3 will be described with reference to FIG. 2.

As illustrated in FIG. 2, the light source device 3 includes a visible light source 31, first and second excitation light sources 32, 33, first to third dichroic mirrors 34 to 36, an optical measurement device 37, a control unit 38, and a memory 39.

The visible light source 31 is a light source used in both the normal observation mode and the fluorescence observation mode, and emits normal light such as white light in a visible wavelength band. In the present embodiment, the visible light source 31 is composed of a light emitting diode (LED) that emits white light (normal light).

The first excitation light source 32 corresponds to a first light source according to the present disclosure. The first excitation light source 32 is a light source used in the fluorescence observation mode and is composed of a semiconductor laser that emits excitation light (hereinafter referred to as "first laser light") having a peak wavelength of about 405 nm. The first laser light is excitation light that excites protoporphyrin biosynthesized in mitochondria when 5-aminolevulinic acid (5-ALA) is taken into cells after being administered into the subject. When excited by the first laser light, the protoporphyrin emits fluorescence having peak wavelengths of about 636 nm and about 705 nm.

The second excitation light source 33 corresponds to the first light source according to the present disclosure. The second excitation light source 33 is a light source used in the fluorescence observation mode and is composed of a semiconductor laser that emits excitation light (hereinafter referred to as "second laser light") in a near-infrared wavelength band (peak wavelength: about 808 nm). The second laser light is excitation light that excites indocyanine green (fluorescent substance). When excited by the second laser light, the indocyanine green emits fluorescence having a peak wavelength (about 835 nm) on a longer wavelength side than the peak wavelength of the second laser light.

In the present embodiment, light (normal light and first and second laser light) emitted from the visible light source 31 and the first and second excitation light sources 32, 33 is designed to be in the classes (laser standard indicating "Safety of Laser Products" (for example, IEC 60825-1: 2014 or 2007)) shown in Tables 1 and 2 below.

TABLE 1

| | Light simultaneously emitted | | | |
| | Normal light | First laser light | Second laser light | None |
|---|---|---|---|---|
| Normal light | — | Class 3R | Class 1 | — |
| First laser light | Class 3R | — | Class 1 | Class 3R |
| Second laser light | Class 1 | Class 1 | — | Class 1 |

TABLE 2

| | Light simultaneously emitted | | | |
| | Normal light | First laser light | Second laser light | None |
|---|---|---|---|---|
| Normal light | — | Class 3R | Class 3R | — |
| First laser light | Class 3R | — | Class 3R | Class 3R |
| Second laser light | Class 3R | Class 3R | — | Class 3R |

Here, Table 1 describes classes of light emitted from the "distal end of the insertion unit 2". For example, as shown in Table 1, when the normal light and the second laser light are simultaneously emitted, the second laser light is designed to be Class 1. For example, when the first and second laser light are simultaneously emitted, the first and second laser light are designed to be Class 1. For example, when only the second laser light is emitted, the second laser light is designed to be Class 1.

Table 2 describes classes of light emitted from the "emission end of the light guide 4". For example, as shown in Table 2, when the normal light and the second laser light are simultaneously emitted, the second laser light is designed to be Class 3R. For example, when the first and second laser light are simultaneously emitted, the first and second laser light are designed to be Class 3R. For example, when only the second laser light is emitted, the second laser light is designed to be Class 3R.

The first dichroic mirror 34 is a dichroic mirror that transmits the first laser light and reflects the second laser light in the same direction as the traveling direction of the first laser light.

The second dichroic mirror 35 is a dichroic mirror that transmits the first and second laser light and reflects the normal light in the same direction as the traveling direction of the first and second laser light.

The third dichroic mirror 36 is a dichroic mirror that transmits the first and second laser light and normal light and reflects measurement light emitted from the optical measurement device 37 in the same direction as the traveling direction of the first and second laser light and the normal light.

Figure 3:
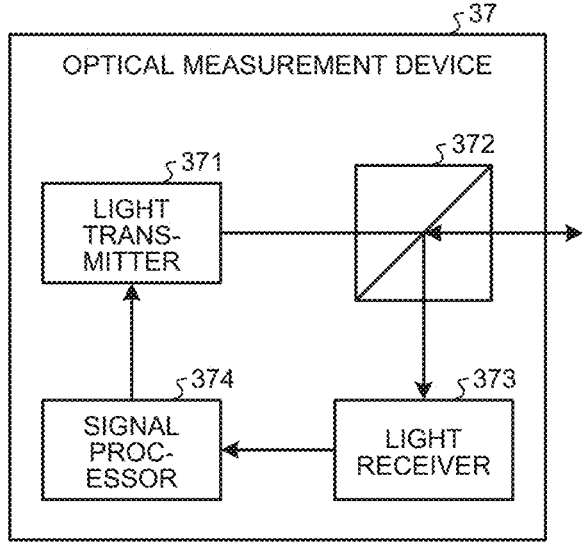
FIG. 3 is a block diagram illustrating a configuration of an optical measurement device.

FIG. 3 is a block diagram illustrating a configuration of the optical measurement device 37.

The optical measurement device 37 is an optical measurement device for measuring a connection state between the light guide 4 and the insertion unit 2 (fiber connection unit 21) with an optical time domain reflectometer (OTDR). As illustrated in FIG. 3, the optical measurement device 37 includes a light transmitter 371, a beam splitter 372, a light receiver 373, and a signal processor 374.

The light transmitter 371 corresponds to a second light source according to the present disclosure. Although not specifically illustrated, the light transmitter 371 is composed of a pulse generator and a semiconductor laser that generates coherent light (measurement light) having a uniform phase, and emits pulsed light of the measurement light under the control of the signal processor 374. The wavelength band of the measurement light is different from the wavelength band of the normal light described above, the wavelength band of the first laser light described above, the wavelength band of fluorescence emitted from protoporphyrin when the protoporphyrin is excited by the first laser light, the wavelength band of the second laser light described above, and the wavelength band of fluorescence emitted from indocyanine green when the indocyanine green is excited by the second laser light. Specifically, the measurement light is laser light having a peak wavelength of about 1310 nm.

Figure 4:
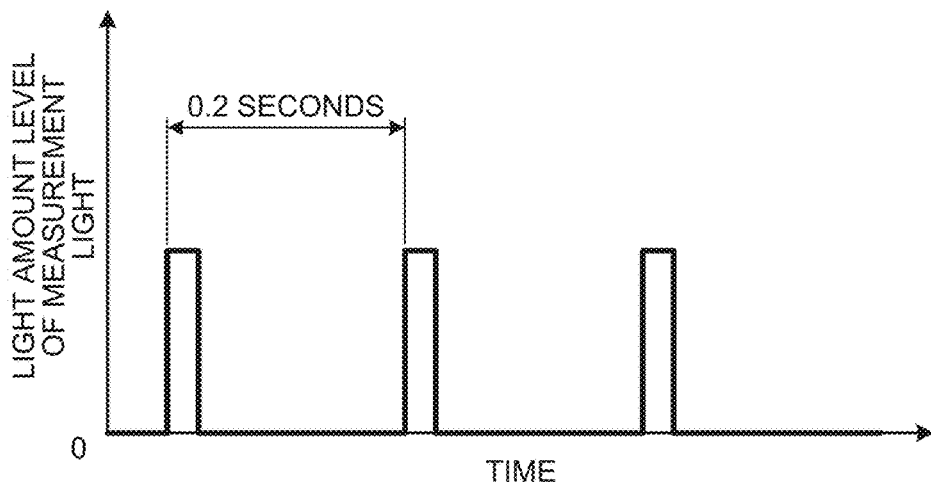
FIG. 4 is a diagram illustrating timing of pulsed light emission of measurement light.

FIG. 4 is a diagram illustrating timing of pulsed light emission of the measurement light.

Under the control of the signal processor 374, the light transmitter 371 causes the measurement light to be emitted in pulses at a cycle less than a time reference corresponding to a class specified in the laser standard indicating the "Safety of Laser Products" to the laser light (first and second laser light) emitted from the emission end of the light guide 4.

Specifically, in the present embodiment, as shown in Table 2, the class of the laser light emitted from the emission end of the light guide 4 is "Class 3R". The time reference corresponding to "Class 3R" is 0.25 seconds. Thus, as illustrated in FIG. 4, the light transmitter 371 causes the measurement light to be emitted in pulses at a cycle of 0.2 seconds which is less than 0.25 seconds.

The beam splitter 372 transmits the measurement light emitted from the light transmitter 371 and advances the measurement light toward the third dichroic mirror 36. The beam splitter 372 reflects return light of the measurement light reflected by the light guide 4 and the like and reflected by the third dichroic mirror 36 toward the light receiver 373.

Although not specifically illustrated, the light receiver 373 includes a photodiode, an amplifier, and an A/D converter, and outputs a signal (digital signal) corresponding to the light amount level of the return light to the signal processor 374.

The signal processor 374 converts the time from when the measurement light is emitted in pulses from the light transmitter 371 to when the return light is received by the light receiver 373 into a distance from the light source device 3, and generates an OTDR waveform indicating the light amount level of the return light with respect to the distance.

Figure 5:
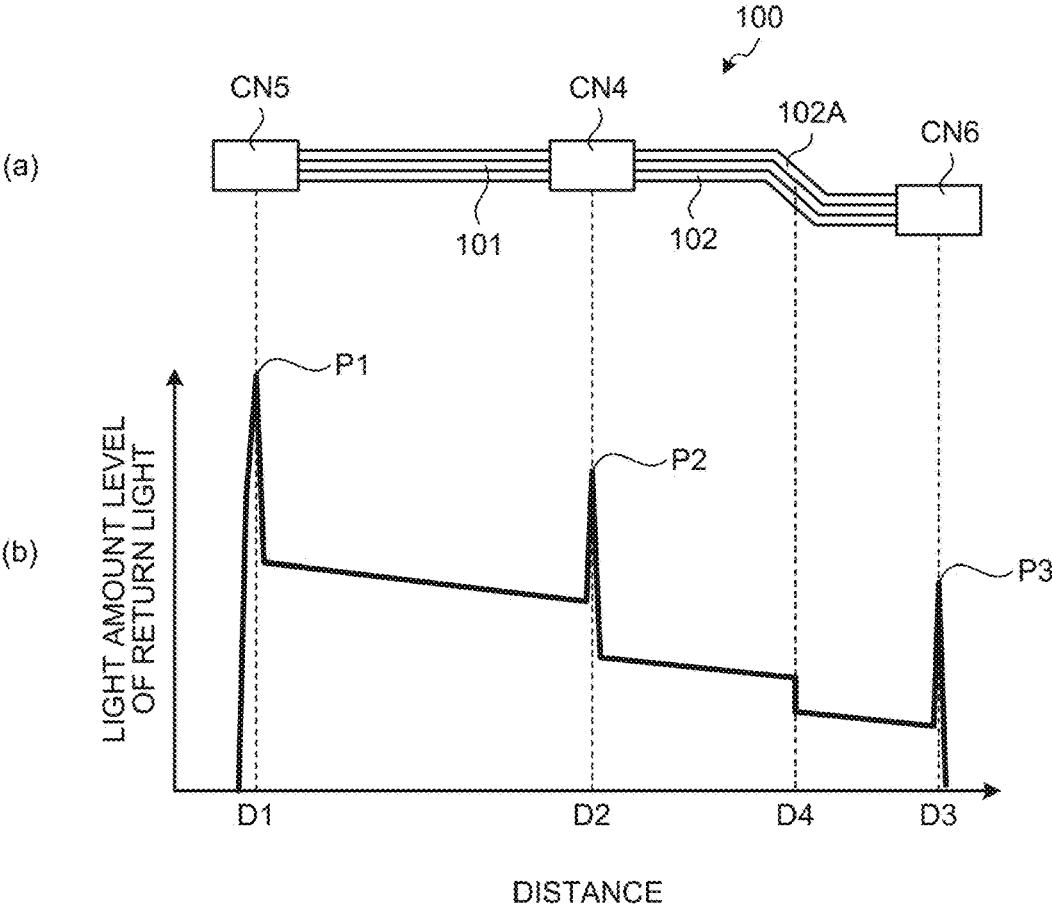
FIG. 5 is a diagram for explaining an OTDR waveform.

FIG. 5 is a diagram for explaining the OTDR waveform. Specifically, (a) of FIG. 5 illustrates an optical fiber 100 connected to the connector CN3 of the light source device 3. (b) of FIG. 5 is a diagram illustrating the OTDR waveform corresponding to the optical fiber 100.

Here, the OTDR waveform will be described by taking an example in which the optical fiber 100 illustrated in FIG. 5 is connected to the connector CN3 of the light source device 3.

As illustrated in FIG. 5, the optical fiber 100 has a configuration in which first and second optical fibers 101, 102 are connected in series by a connector CN4, and connectors CN5 and CN6 are provided at both ends, respectively. The connector CN5 is connected to the connector CN3 of the light source device 3.

When the measurement light emitted from the light source device 3 passes through the connectors CN3 to CN5, Fresnel reflection occurs in each of the connectors CN3 to CN5. When the measurement light travels through each of the first and second optical fibers 101, 102, Rayleigh scattering occurs.

Thus, in the OTDR waveform corresponding to the optical fiber 100, as illustrated in (b) of FIG. 5, peaks P1 to P3 of the light amount level of the return light corresponding to the Fresnel reflection are present in distances D1 to D3, which are respective distances from the light source device 3 to the connectors CN3 to CN5. In the OTDR waveform corresponding to the optical fiber 100, the return light corresponding to Rayleigh scattering is detected between the distance D1 and the distance D2 corresponding to the position of the first optical fiber 101 and between the distance D2 and the distance D3 corresponding to the position of the second optical fiber 102, and the light amount level of the return light gradually decreases as the distance increases. When the second optical fiber 102 has a bent portion 102A ((a) of FIG. 5), the light amount level of the return light rapidly decreases at the distance D4 from the light source device 3 to the portion 102A in the OTDR waveform corresponding to the optical fiber 100.

The control unit 38 is realized by executing various programs stored in the memory 39 by a controller such as a CPU or a micro processing unit (MPU), and controls the entire operation of the light source device 3. The control unit 38 is not limited to the CPU or the MPU, and may be composed of an integrated circuit such as an application specific integrated circuit (ASIC) or an FPGA.

The control unit 38 drives a light source designated by the control device 9 among the visible light source 31 and the first and second excitation light sources 32, 33 according to the control signal output from the control device 9. At this time, the control unit 38 executes specific lighting drive control.

Details of the lighting drive control will be described later.

The memory 39 stores a program executed by the control unit 38, information necessary for processing of the control unit 38, and the like.

Next, the lighting drive control executed by the control unit 38 described above will be described.

Here, in describing the lighting drive control, the following first to third combinations are assumed as an appropriate combination of the light guide 4 and the insertion unit 2.

The first combination is a combination in which the insertion unit 2 (part 1) having a diameter of 10 mm is connected to the light guide 4 having a diameter of 5 mm.

The second combination is a combination in which the insertion unit 2 (part 2) having a diameter of 10 mm is connected to the light guide 4 having a diameter of 2 mm.

The third combination is a combination in which the insertion unit 2 having a diameter of 5 mm is connected to the light guide 4 having a diameter of 1 mm.

In the light guide 4 having a diameter of 5 mm in the first combination, the light guide 4 having a diameter of 2 mm in the second combination, and the light guide 4 having a diameter of 1 mm in the third combination, optical fibers (not illustrated) provided inside are different from each other. In the insertion unit 2 (part 1) having a diameter of 10 mm in the first combination, the insertion unit 2 (part 2) having a diameter of 10 mm in the second combination, and the insertion unit 2 having a diameter of 5 mm in the third combination, the optical fiber 22 and the concave lens 23 provided inside are different from each other.

Information indicating first to third OTDR waveforms measured in advance by the optical measurement device 37 is stored in advance in the memory 39.

Figure 6:
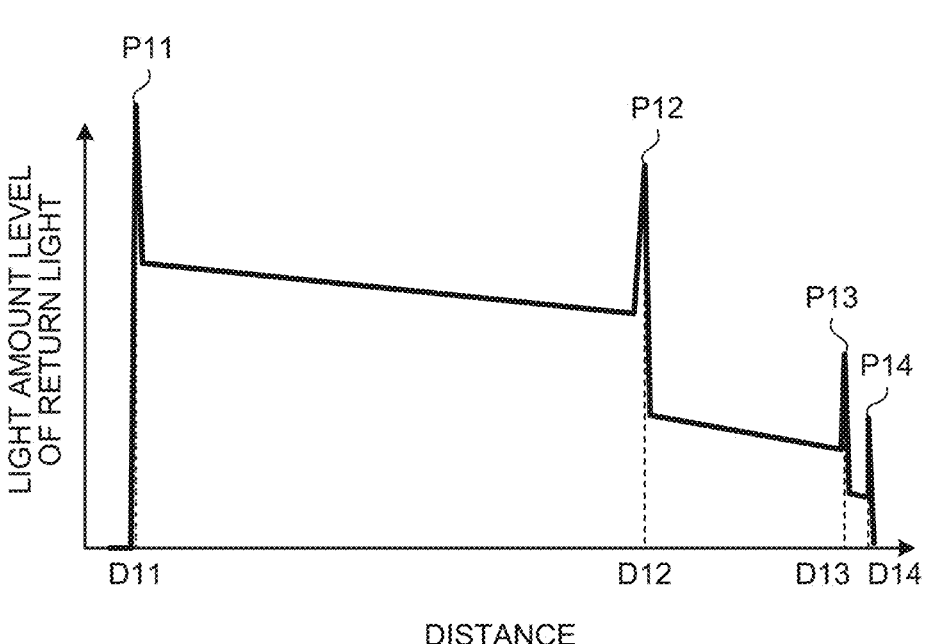
FIG. 6 is a diagram illustrating a first OTDR waveform.
Figure 7:
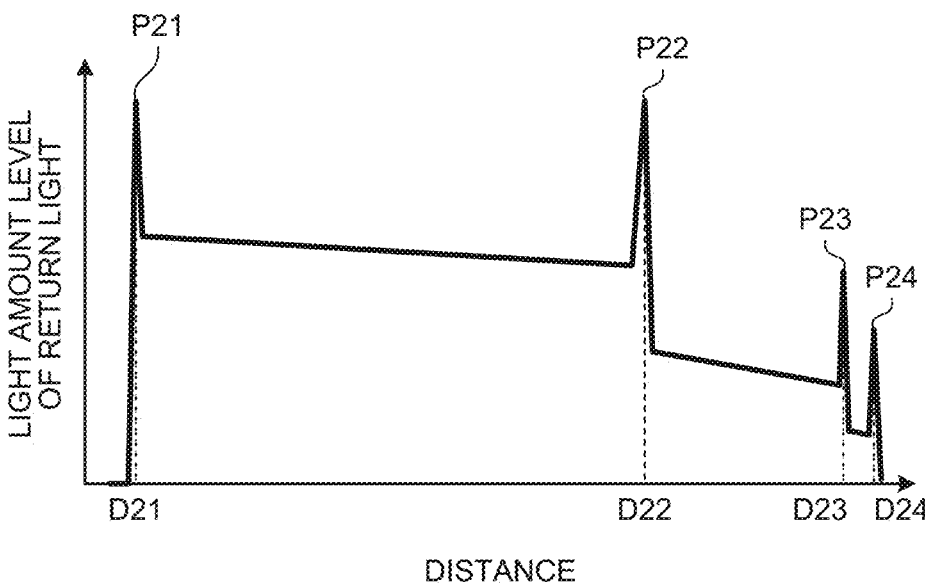
FIG. 7 is a diagram illustrating a second OTDR waveform.
Figure 8:
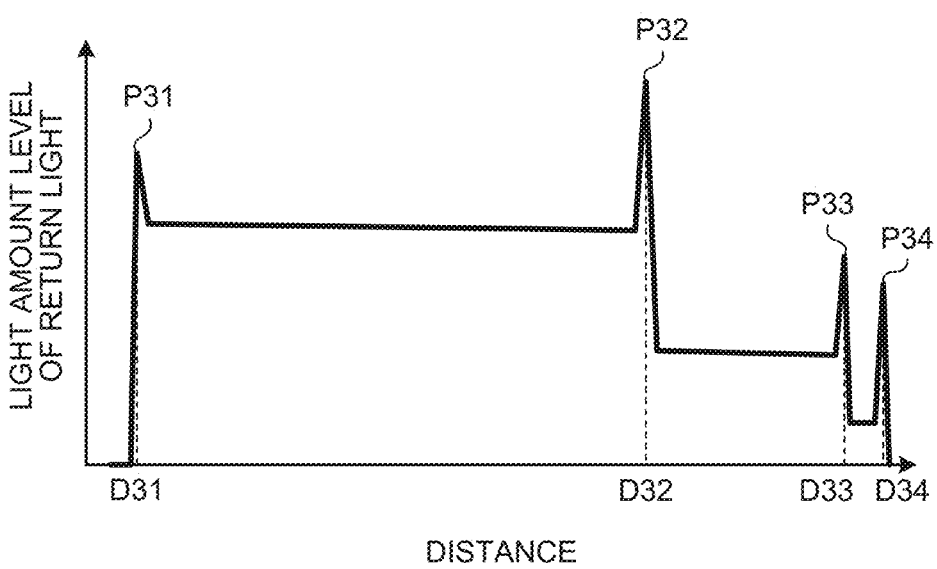
FIG. 8 is a diagram illustrating a third OTDR waveform.

FIGS. 6 to 8 are diagrams illustrating the first to third OTDR waveforms, respectively.

The first OTDR waveform illustrated in FIG. 6 is an OTDR waveform measured by the optical measurement device 37 in a state where the light guide 4 and the insertion unit 2 of the first combination are connected to the light source device 3.

In the first OTDR waveform, peaks P11 to P14 are present at the distances D11 to D14, respectively. The peak P11 at the distance D11 is a peak corresponding to Fresnel reflection at the connector CN1. The peak P12 at the distance D12 is a peak corresponding to Fresnel reflection at the fiber connection unit 21. The peak P13 at the distance D13 is a peak corresponding to Fresnel reflection on the incident surface of the concave lens 23. The peak P14 at the distance D14 is a peak corresponding to Fresnel reflection on the emission surface of the concave lens 23.

The information indicating that the peaks P11 to P14 are present at the distances D11 to D14 and the information indicating that the number of the peaks P11 to P14 is four are characteristics unique to the first combination, and are stored in the memory 39 as information indicating the first OTDR waveform.

The change in the light amount level of the return light between the distance D11 and the distance D12 corresponds to Rayleigh scattering in the optical fiber in the light guide 4 having a diameter of 5 mm of the first combination, and it exhibits a behavior unique to the optical fiber. The information (gradient or change amount) indicating the change in the light amount level of the return light between the distance D11 and the distance D12 is a characteristic unique to the first combination, and is stored in the memory 39 as information indicating the first OTDR waveform with a specific width around the information (gradient or change amount).

Further, the change in the light amount level of the return light between the distance D12 and the distance D13 corresponds to Rayleigh scattering in the optical fiber 22 in the insertion unit 2 (part 1) having a diameter of 10 mm of the first combination, and it exhibits a behavior unique to the optical fiber 22. The information (gradient or change amount) indicating the change in the light amount level of the return light between the distance D12 and the distance D13 is a characteristic unique to the first combination, and is stored in the memory 39 as information indicating the first OTDF waveform with a specific width around the information (gradient or change amount).

The change in the light amount level of the return light between the distance D13 and the distance D14 corresponds to Rayleigh scattering at the concave lens 23 in the insertion unit 2 (part 1) having a diameter of 10 mm of the first combination, and it exhibits a behavior unique to the concave lens 23. The information (gradient or change amount) indicating the change in the light amount level of the return light between the distance D13 and the distance D14 is a characteristic unique to the first combination, and is stored in the memory 39 as information indicating the first OTDF waveform with a specific width around the information (gradient or change amount).

The second OTDR waveform illustrated in FIG. 7 is an OTDR waveform measured by the optical measurement device 37 in a state where the light guide 4 and the insertion unit 2 of the second combination are connected to the light source device 3.

In the second OTDR waveform, peaks P21 to P24 are present at the distances D21 to D24, respectively. The peak P21 at the distance D21 is a peak corresponding to Fresnel reflection at the connector CN1. The peak P22 at the distance D22 is a peak corresponding to Fresnel reflection at the fiber connection unit 21. The peak P23 at the distance D23 is a peak corresponding to Fresnel reflection on the incident surface of the concave lens 23. The peak P24 at the distance D24 is a peak corresponding to Fresnel reflection on the emission surface of the concave lens 23.

The information indicating that the peaks P21 to P24 are present at the distances D21 to D24 and the information indicating that the number of the peaks P21 to P24 is four are characteristics unique to the second combination, and are stored in the memory 39 as information indicating the second OTDR waveform.

The change in the light amount level of the return light between the distance D21 and the distance D22 corresponds to Rayleigh scattering in the optical fiber in the light guide 4 having a diameter of 2 mm of the second combination, and it exhibits a behavior unique to the optical fiber. The information (gradient or change amount) indicating the change in the light amount level of the return light between the distance D21 and the distance D22 is a characteristic unique to the second combination, and is stored in the memory 39 as information indicating the second OTDR waveform with a specific width around the information (gradient or change amount).

Further, the change in the light amount level of the return light between the distance D22 and the distance D23 corresponds to Rayleigh scattering in the optical fiber 22 in the insertion unit 2 (part 2) having a diameter of 10 mm of the second combination, and it exhibits a behavior unique to the optical fiber 22. The information (gradient or change amount) indicating the change in the light amount level of the return light between the distance D22 and the distance D23 is a characteristic unique to the second combination, and is stored in the memory 39 as information indicating the second OTDR waveform with a specific width around the information (gradient or change amount).

The change in the light amount level of the return light between the distance D23 and the distance D24 corresponds to Rayleigh scattering at the concave lens 23 in the insertion unit 2 (part 2) having a diameter of 10 mm of the second combination, and it exhibits a behavior unique to the concave lens 23. The information (gradient or change amount) indicating the change in the light amount level of the return light between the distance D23 and the distance D24 is a characteristic unique to the second combination, and is stored in the memory 39 as information indicating the second OTDR waveform with a specific width around the information (gradient or change amount).

The third OTDR waveform illustrated in FIG. 8 is an OTDR waveform measured by the optical measurement device 37 in a state where the light guide 4 and the insertion unit 2 of the third combination are connected to the light source device 3.

In the third OTDR waveform, peaks P31 to P34 are present at the distances D31 to D34, respectively. The peak P31 at the distance D31 is a peak corresponding to Fresnel reflection at the connector CN1. The peak P32 at the distance D32 is a peak corresponding to Fresnel reflection at the fiber connection unit 21. The peak P33 at the distance D33 is a peak corresponding to Fresnel reflection on the incident surface of the concave lens 23. The peak P34 at the distance D34 is a peak corresponding to Fresnel reflection on the emission surface of the concave lens 23.

The information indicating that the peaks P31 to P34 are present at the distances D31 to D34 and the information indicating that the number of the peaks P31 to P34 is four are characteristics unique to the third combination, and are stored in the memory 39 as information indicating the third OTDR waveform.

The change in the light amount level of the return light between the distance D31 and the distance D32 corresponds to Rayleigh scattering in the optical fiber in the light guide 4 having a diameter of 1 mm of the third combination, and it exhibits a behavior unique to the optical fiber. The information (gradient or change amount) indicating the change in the light amount level of the return light between the distance D31 and the distance D32 is a characteristic unique to the third combination, and is stored in the memory 39 as information indicating the third OTDR waveform with a specific width around the information (gradient or change amount).

Further, the change in the light amount level of the return light between the distance D32 and the distance D33 corresponds to Rayleigh scattering in the optical fiber 22 in the insertion unit 2 having a diameter of 5 mm of the third combination, and it exhibits a behavior unique to the optical fiber 22. The information (gradient or change amount) indicating the change in the light amount level of the return light between the distance D32 and the distance D33 is a characteristic unique to the third combination, and is stored in the memory 39 as information indicating the third OTDR waveform with a specific width around the information (gradient or change amount).

The change in the light amount level of the return light between the distance D33 and the distance D34 corresponds to Rayleigh scattering at the concave lens 23 in the insertion unit 2 having a diameter of 5 mm of the third combination, and it exhibits a behavior unique to the concave lens 23. The information (gradient or change amount) indicating the change in the light amount level of the return light between the distance D33 and the distance D34 is a characteristic unique to the third combination, and is stored in the memory 39 as information indicating the third OTDR waveform with a specific width around the information (gradient or change amount).

Figure 9:
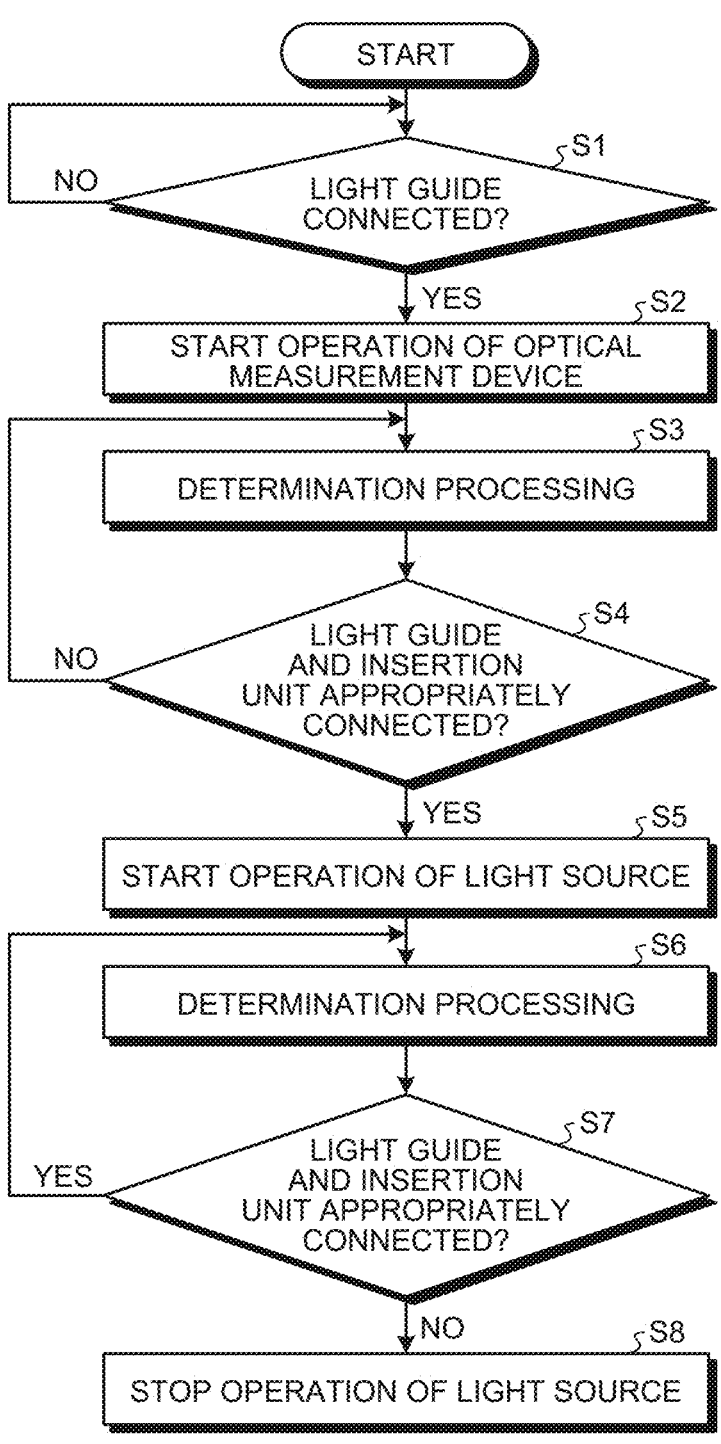
FIG. 9 is a flowchart illustrating lighting drive control executed by a control unit.
Figure 10:
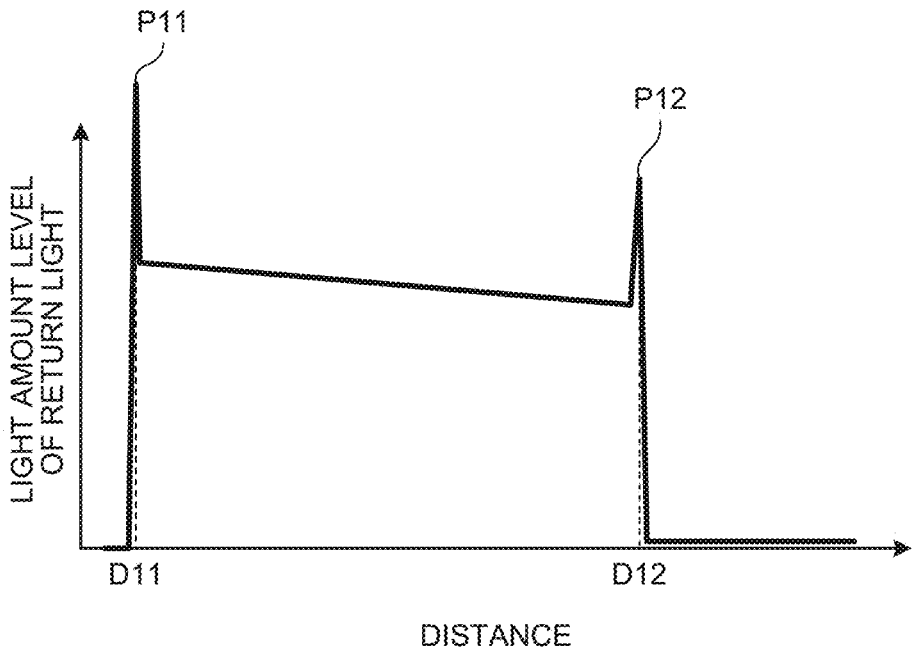
FIG. 10 is a diagram for explaining lighting drive control executed by the control unit.
Figure 11:
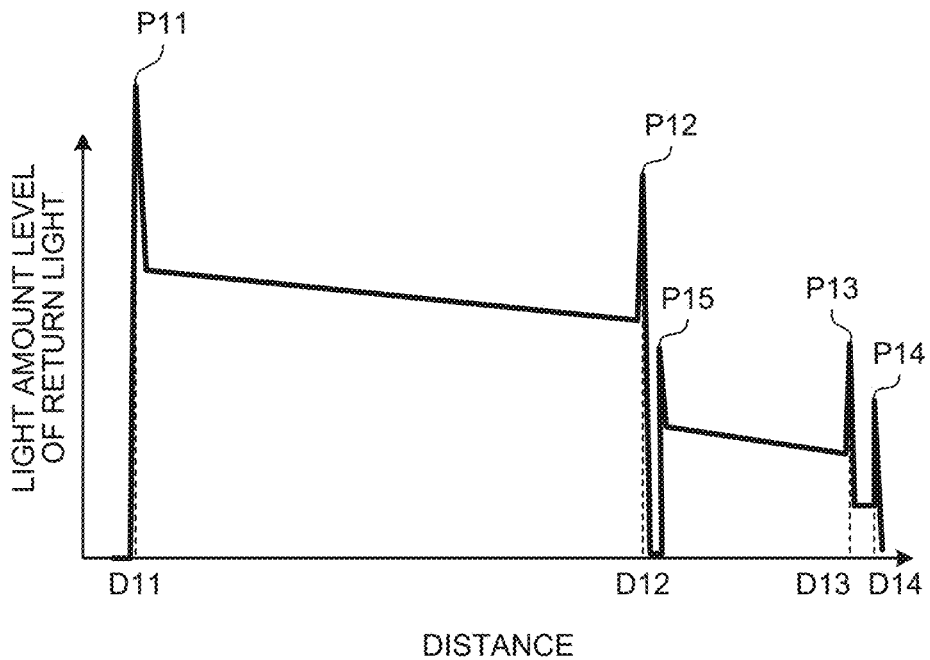
FIG. 11 is a diagram for explaining lighting drive control executed by the control unit.
Figure 12:
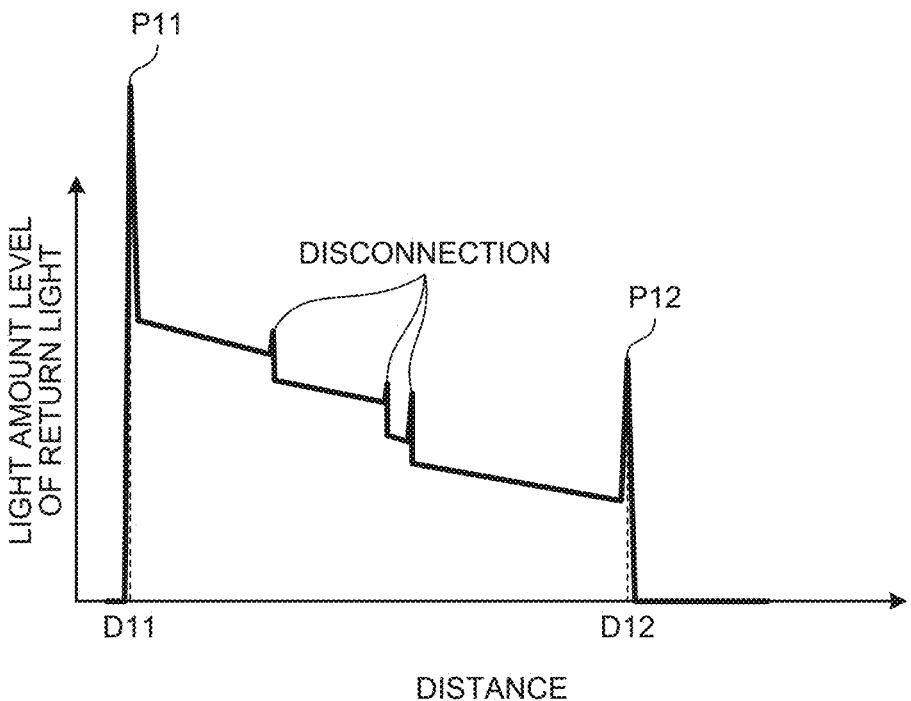
FIG. 12 is a diagram illustrating a modification of the embodiment.

FIG. 9 is a flowchart illustrating lighting drive control executed by the control unit 38. FIGS. 10 to 12 are diagrams for explaining lighting drive control executed by the control unit 38.

First, the control unit 38 constantly monitors whether the connection of the light guide 4 to the light source device 3 has been detected by a detection unit (not illustrated) (Step S1).

When it is determined that the connection of the light guide 4 to the light source device 3 has been detected (Step S1: Yes), the control unit 38 starts the operation of the optical measurement device 37 (Step S2). This causes the optical measurement device 37 (signal processor 374) to start generating an OTDR waveform.

After Step S2, the control unit 38 executes the following determination processing of determining whether the light guide 4 and the insertion unit 2 are appropriately connected based on the information indicating the first to third OTDR waveforms stored in the memory 39 and the OTDR waveform generated by the optical measurement device 37 (Step S3).

Here, the determination processing executed in Step S3 includes first and second determination processing.

The first determination processing is as follows.

The control unit 38 determines whether the light guide 4 and the insertion unit 2 are appropriately connected based on the information indicating the first to third OTDR waveforms stored in the memory 39 and the information indicating the peak in the OTDR waveform generated by the optical measurement device 37.

Specifically, in the first determination processing, the control unit 38 determines whether there are peaks P11 to P14 at the distances D11 to D14, respectively, in the OTDR waveform generated by the optical measurement device 37, based on the information indicating the first OTDR waveform. The control unit 38 also determines whether the number of peaks in the OTDR waveform generated by the optical measurement device 37 is four, which is the number of peaks based on the information indicating the first OTDR waveform.

In the first determination processing, the control unit 38 also determines whether there are peaks P21 to P24 at the distances D21 to D24, respectively, in the OTDR waveform generated by the optical measurement device 37, based on the information indicating the second OTDR waveform. The control unit 38 also determines whether the number of peaks in the OTDR waveform generated by the optical measurement device 37 is four, which is the number of peaks based on the information indicating the second OTDR waveform.

Further, in the first determination processing, the control unit 38 determines whether there are peaks P31 to P34 at the distances D31 to D34, respectively, in the OTDR waveform generated by the optical measurement device 37, based on the information indicating the third OTDR waveform. The control unit 38 also determines whether the number of peaks in the OTDR waveform generated by the optical measurement device 37 is four, which is the number of peaks based on the information indicating the third OTDR waveform.

Then, the control unit 38 determines "Yes" in the first determination processing when the number of peaks in the OTDR waveform is four, and peaks P11 to P14 are present at the distances D11 to D14, respectively, peaks P21 to P24 are present in the distances D21 to D24, respectively, or peaks P31 to P34 are present in the distances D31 to D34, respectively, in the OTDR waveform generated by the optical measurement device 37. The control unit 38 determines "No" in the first determination processing in other cases.

The second determination processing is as follows.

The control unit 38 determines whether the light guide 4 and the insertion unit 2 are appropriately connected based on the information indicating the first to third OTDR waveforms stored in the memory 39 and the information indicating the change in the light amount level of the return light within the range defined by the specific distance in the OTDR waveform generated by the optical measurement device 37.

Specifically, in the second determination processing, the control unit 38 determines whether the OTDR waveform generated by the optical measurement device 37 satisfies all of the following first conditions (1) to (3).

(1) Information (gradient or change amount) indicating the change in the light amount level of the return light between the distance D11 and the distance D12 in the OTDR waveform generated by the optical measurement device 37 falls within a specific width with the information (gradient or change amount) indicating the change in the light amount level of the return light between the distance D11 and the distance D12 based on the information indicating the first OTDR waveform being centered.

(2) Information (gradient or change amount) indicating the change in the light amount level of the return light between the distance D12 and the distance D13 in the OTDR waveform generated by the optical measurement device 37 falls within a specific width with the information (gradient or change amount) indicating the change in the light amount level of the return light between the distance D12 and the distance D13 based on the information indicating the first OTDR waveform being centered.

(3) Information (gradient or change amount) indicating the change in the light amount level of the return light between the distance D13 and the distance D14 in the OTDR waveform generated by the optical measurement device 37 falls within a specific width with the information (gradient or change amount) indicating the change in the light amount level of the return light between the distance D13 and the distance D14 based on the information indicating the first OTDR waveform being centered.

In the second determination processing, the control unit 38 also determines whether the OTDR waveform generated by the optical measurement device 37 satisfies all of the following second conditions (4) to (6).

(4) Information (gradient or change amount) indicating the change in the light amount level of the return light between the distance D21 and the distance D22 in the OTDR waveform generated by the optical measurement device 37 falls within a specific width with the information (gradient or change amount) indicating the change in the light amount level of the return light between the distance D21 and the distance D22 based on the information indicating the second OTDR waveform being centered.

(5) Information (gradient or change amount) indicating the change in the light amount level of the return light between the distance D22 and the distance D23 in the OTDR waveform generated by the optical measurement device 37 falls within a specific width with the information (gradient or change amount) indicating the change in the light amount level of the return light between the distance D22 and the distance D23 based on the information indicating the second OTDR waveform being centered.

(6) Information (gradient or change amount) indicating the change in the light amount level of the return light between the distance D23 and the distance D24 in the OTDR waveform generated by the optical measurement device 37 falls within a specific width with the information (gradient or change amount) indicating the change in the light amount level of the return light between the distance D23 and the distance D24 based on the information indicating the second OTDR waveform being centered.

Further, in the second determination processing, the control unit 38 determines whether the OTDR waveform generated by the optical measurement device 37 satisfies all of the following third conditions (7) to (9).

(7) Information (gradient or change amount) indicating the change in the light amount level of the return light between the distance D31 and the distance D32 in the OTDR waveform generated by the optical measurement device 37 falls within a specific width with the information (gradient or change amount) indicating the change in the light amount level of the return light between the distance D31 and the distance D32 based on the information indicating the third OTDR waveform being centered.

(8) Information (gradient or change amount) indicating the change in the light amount level of the return light between the distance D32 and the distance D33 in the OTDR waveform generated by the optical measurement device 37 falls within a specific width with the information (gradient or change amount) indicating the change in the light amount level of the return light between the distance D32 and the distance D33 based on the information indicating the third OTDR waveform being centered.

(9) Information (gradient or change amount) indicating the change in the light amount level of the return light between the distance D33 and the distance D34 in the OTDR waveform generated by the optical measurement device 37 falls within a specific width with the information (gradient or change amount) indicating the change in the light amount level of the return light between the distance D33 and the distance D34 based on the information indicating the third OTDR waveform being centered.

Then, the control unit 38 determines "Yes" in the second determination processing when the OTDR waveform generated by the optical measurement device 37 satisfies all of the first conditions, all of the second conditions, or all of the third conditions. The control unit 38 determines "No" in the second determination processing in other cases.

As a result of the determination processing (Step S3), when it is determined as "No" in either the first or second determination processing, it is determined that the light guide 4 and the insertion unit 2 are not appropriately connected (Step S4: No), and the control unit 38 returns to Step S3.

For example, FIG. 10 illustrates an OTDR waveform generated by the optical measurement device 37 in a state where the light guide 4 having a diameter of 5 mm is connected to the light source device 3 but the insertion unit 2 is not connected to the light guide 4.

The number of peaks in the OTDR waveform illustrated in FIG. 10 is two, which is not the same as the number of peaks (four) based on the information indicating the first to third OTDR waveforms. Thus, as a result of the determination processing (Step S3), the control unit 38 determines "No" in the first determination processing and determines that the light guide 4 and the insertion unit 2 are not appropriately connected (Step S4: No).

For example, FIG. 11 illustrates an OTDR waveform generated by the optical measurement device 37 in a state where the light guide 4 having a diameter of 5 mm is connected to the light source device 3 and the insertion unit 2 (part 1) having a diameter of 10 mm is connected to the light guide 4, but the light guide 4 and the insertion unit 2 are not appropriately connected.

In the OTDR waveform illustrated in FIG. 11, as a result of the light guide 4 and the insertion unit 2 not being appropriately connected, a new peak P15 that is not a characteristic unique to the first combination described above appears in the vicinity of the distance D12, and the number of peaks is five, which is not the same as the number of peaks (four) based on the information indicating the first to third OTDR waveforms. Thus, as a result of the determination processing (Step S3), the control unit 38 determines "No" in the first determination processing and determines that the light guide 4 and the insertion unit 2 are not appropriately connected (Step S4: No).

On the other hand, when it is determined as "Yes" in both the first and second determination processing as a result of the determination processing (Step S3), it is determined that the light guide 4 and the insertion unit 2 are appropriately connected (Step S4: Yes), and the control unit 38 starts the operation of the light source designated by the control device 9 among the visible light source 31 and the first and second excitation light sources 32, 33 according to the control signal output from the control device 9 (Step S5). This causes the light source to emit light (at least one of normal light and first and second laser light).

After Step S5, the control unit 38 executes the same determination processing as in Step S3 (Step S6).

As a result of the determination processing (Step S6), when it is determined as "Yes" in both the first and second determination processing, it is determined that the light guide 4 and the insertion unit 2 are appropriately connected (Step S7: Yes), and the control unit 38 returns to Step S6.

When it is determined as "No" in either the first or second determination processing as a result of the determination processing (Step S6), it is determined that the light guide 4 and the insertion unit 2 are not appropriately connected (Step S7: No), and the control unit 38 stops the operation of the light source that has started its operation in Step S5 (Step S8). This causes the light source to stop emitting light (at least one of normal light and first and second laser light).

For example, when the light guide 4 and the insertion unit 2 of the above-described first combination are connected to the light source device 3, but the light guide 4 is detached from the insertion unit 2 by an external force, the optical measurement device 37 generates the OTDR waveform illustrated in FIG. 10. As a result of the determination processing (Step S6), the control unit 38 determines "No" in the first determination processing, and thus the control unit 38 determines that the light guide 4 and the insertion unit 2 are not appropriately connected (Step S7: No), and stops outputting light from the light source (Step S8).

For example, when the light guide 4 and the insertion unit 2 of the above-described first combination are connected to the light source device 3, but the light guide 4 is not appropriately connected to the insertion unit 2 because of an external force, the optical measurement device 37 generates the OTDR waveform illustrated in FIG. 11. As a result of the determination processing (Step S6), the control unit 38 determines "No" in the first determination processing, and thus the control unit 38 determines that the light guide 4 and the insertion unit 2 are not appropriately connected (Step S7: No), and stops outputting light from the light source (Step S8).

According to the present embodiment described above, the following effects are obtained.

In the light source device 3 according to the present embodiment, the control unit 38 determines whether the light guide 4 and the insertion unit 2 are appropriately connected based on the return light of the measurement light emitted from the light transmitter 371. Then, the control unit 38 controls the output of the first and second laser light in the first and second excitation light sources 32, 33 based on the determination result.

Thus, when the light guide 4 and the insertion unit 2 are not appropriately connected, such as when the light guide 4 is detached from the insertion unit 2, the output of the first and second laser light may be stopped. That is, as a result of such a configuration, it is possible to design the laser light emitted from the distal end of the insertion unit 2 to satisfy the requirement defined in the laser standard indicating the "Safety of Laser Products". Then, the first and second laser light emitted from the emission end of the light guide 4 may have a high light amount such as Class 3R, and as a result, it is possible to secure the light amounts of the first and second laser light to be emitted from the distal end of the insertion unit 2.

Thus, according to the light source device 3 of the present embodiment, it is possible to secure the light amount of laser light emitted to a subject while securing safety.

In the light source device 3 according to the present embodiment, the control unit 38 determines whether the light guide 4 and the insertion unit 2 are appropriately connected based on the OTDR waveform (information indicating a peak in the OTDR waveform or information indicating a change in the light amount level of the return light within a range defined by a specific distance in the OTDR waveform) generated by the optical measurement device 37.

Thus, it is possible to easily and highly accurately determine whether the light guide 4 and the insertion unit 2 are appropriately connected with a simple configuration.

In the light source device 3 according to the present embodiment, the light transmitter 371 causes the measurement light to be emitted in pulses at a cycle less than a time reference corresponding to a class specified in the laser standard indicating the "Safety of Laser Products" to the laser light (first and second laser light) emitted from the emission end of the light guide 4.

Thus, when the light guide 4 is detached from the insertion unit 2, it is possible to detect that the light guide 4 is detached from the insertion unit 2 based on the measurement light emitted from the light transmitter 371 before the first and second laser light are emitted from the emission end of the light guide 4 by the time reference, and to stop the output of the first and second laser light. Thus, it is possible to sufficiently ensure safety.

In the light source device 3 according to the present embodiment, the wavelength band of the measurement light is different from the wavelength band of the normal light, the wavelength band of the first laser light, the wavelength band of fluorescence emitted from protoporphyrin when the protoporphyrin is excited by the first laser light, the wavelength band of the second laser light, and the wavelength band of fluorescence emitted from indocyanine green when the indocyanine green is excited by the second laser light.

Thus, the measurement light does not disturb various kinds of observation in the normal observation mode or the fluorescence observation mode.

Although the embodiment for carrying out the present disclosure has been described so far, the present disclosure should not be limited only by the above-described embodiment.

In the above-described embodiment, the connection state between the light guide 4 and the insertion unit 2 is measured by the OTDR, but the present disclosure is not limited to this configuration. Other configurations may be adopted as long as the connection state between the light guide 4 and the insertion unit 2 is measured based on return light of the measurement light. For example, a configuration may be adopted in which the connection state between the light guide 4 and the insertion unit 2 is measured based on a value obtained by integrating return light of the measurement light without using the OTDR waveform.

In the above-described embodiment, two of first and second excitation light sources 32, 33 are provided as the first light source according to the present disclosure, but the present disclosure is not limited to this configuration. The number of the first light sources according to the present disclosure is not limited to two, and may be one or three or more.

In the above-described embodiment, the light source device 3 according to the present disclosure is mounted on the medical observation system 1 in which the insertion unit 2 is composed of a rigid endoscope, but the present disclosure is not limited to this configuration. For example, the light source device 3 according to the present disclosure may be mounted on a surgical microscope (see, for example, JP 2016-42981 A and WO 2017/065018) to enlarge and observe a predetermined visual field area in a subject (in a living body) or a subject surface (living body surface).

In the above-described embodiment, in Step S8, the control unit 38 stops the operation of the light source that has started its operation in Step S5, but the present disclosure is not limited to this configuration. The light amount may be reduced to a light amount that may ensure safety without stopping the light output.

In the above-described embodiment, when only normal light is emitted from the visible light source 31, the lighting drive control described above does not have to be executed because normal light is different from laser light which requires consideration for safety. That is, after determining that the connection of the light guide 4 to the light source device 3 has been detected (Step S1: Yes), the control unit 38 may start the operation of the visible light source 31 in Step S5 without executing the determination processing (Step S3) or the like.

In addition, in the above-described embodiment, when the normal light and at least one of the first and second laser light are simultaneously emitted, only the output of the laser light may be stopped in Step S8.

In the above-described embodiment, in at least one of the case of determining "No" in Step S4 and the case of determining "No" in Step S7, the control unit 38 may cause an external notification unit to notify warning information indicating that the light guide 4 and the insertion unit 2 are not appropriately connected. For example, the control unit 38 causes the display device 7 as a notification unit to display the warning information via the control device 9. The notification unit according to the present disclosure is not limited to the display device 7, and other display devices, speakers that output the warning information by voice, and the like may be adopted.

Then, the user such as a doctor may recognize that the light guide 4 and the insertion unit 2 are not appropriately connected by recognizing the warning information. Thus, convenience may improve.

In the above-described embodiment, both the first and second determination processing are executed as the determination processing (Steps S3, S6), but the present disclosure is not limited to this configuration, and only the first determination processing may be executed. That is, in Steps S4 and S7, as a result of the determination processing (Steps S3, S6), the control unit 38 determines that the light guide 4 and the insertion unit 2 are not appropriately connected (Steps S4, S7: No) when it is determined as "No" in the first determination processing, and determines that the light guide 4 and the insertion unit 2 are appropriately connected (Steps S4, S7: Yes) when it is determined as "Yes" in the first determination processing.

Meanwhile, when the optical fiber in the light guide 4, the optical fiber 22 in the insertion unit 2, or the concave lens 23 deteriorates over time, the light amount level of the return light of the portion decreases. That is, it is easily determined as "No" in the second determination processing. Thus, in the above-described embodiment, when it is determined as "No" in the second determination processing, the control unit 38 may cause an external notification unit to notify warning information indicating that the optical fiber in the light guide 4, the optical fiber 22 in the insertion unit 2, and the like are deteriorated over time. Examples of the notification unit include the above-described display device 7, a display device other than the display device 7, and a speaker that outputs the warning information by voice.

FIG. 12 is a diagram illustrating a modification of the embodiment. Specifically, FIG. 12 illustrates an OTDR waveform generated by the optical measurement device 37 in a state where the light guide 4 having a diameter of 5 mm is connected to the light source device 3, but the insertion unit 2 is not connected to the light guide 4, and the optical fiber in the light guide 4 is disconnected.

For example, when the disconnection is occurred in the optical fiber in the light guide 4, as illustrated in FIG. 12, the light amount level of the return light rapidly decreases at the distance where the disconnection is occurred. As a result, it is easily determined as "No" in the second determination processing. Then, when the control unit 38 determines "No" in the second determination processing, the control unit 38 causes an external notification unit to notify warning information.

When a foreign matter or dirt is attached to the end surface of the light guide 4 or when the incident surface or the emission surface of the concave lens 23 is fogged, in the OTDR waveform generated by the optical measurement device 37, a large peak of the light amount level of the return light compared to the normal state is obtained at a distance corresponding to the end surface of the light guide 4 or the incident surface or the emission surface of the concave lens 23. Thus, in such a case, the control unit 38 may cause an external notification unit to notify warning information indicating that a foreign matter or dirt is attached or fogging is occurred. Examples of the notification unit include the above-described display device 7, a display device other than the display device 7, and a speaker that outputs the warning information by voice. When the incident surface or the emission surface of the concave lens 23 is fogged, the control unit 38 may operate a heater (not illustrated) to apply heat to the concave lens 23 to remove the fog.

The following configurations also belong to the technical scope of the present disclosure.

(1) A medical light source device including: a first light source configured to emit laser light; a second light source configured to emit measurement light for measuring a connection state between a light guide configured to guide the laser light and an emission optical system configured to irradiate a subject with the laser light through the light guide to the light guide; and a control unit configured to control output of the laser light in the first light source based on return light of the measurement light emitted from the second light source.

(2) The medical light source device according to (1), further including an optical measurement device configured to measure the connection state by using an optical time domain reflectometer (OTDR), the optical measurement device including the second light source and being configured to generate an OTDR waveform indicating a light amount level of the return light with respect to a distance from the medical light source device, wherein the control unit is configured to control output of the laser light in the first light source based on the OTDR waveform.

(3) The medical light source device according to (2), wherein the control unit is configured to control output of the laser light in the first light source based on information indicating a peak in the OTDR waveform.

(4) The medical light source device according to (3), wherein the control unit is configured to determine whether there is a peak of the light amount level of the return light at a specific distance from the medical light source device based on the OTDR waveform, and control output of the laser light in the first light source based on a result of the determination.

(5) The medical light source device according to (3) or (4), wherein the control unit is configured to determine whether number of peaks in the OTDR waveform is a specific number, and control output of the laser light in the first light source based on a result of the determination.

(6) The medical light source device according to any one of (2) to (5), wherein the control unit is configured to control output of the laser light in the first light source based on information indicating a change in the light amount level of the return light within a range defined by a specific distance from the medical light source device in the OTDR waveform.

(7) The medical light source device according to any one of (1) to (6), wherein the control unit is configured to cause, based on the return light, a notification unit to notify warning information indicating a warning.

(8) The medical light source device according to any one of (1) to (7), wherein the second light source is configured to cause the measurement light to be emitted in pulses at a cycle less than a time reference corresponding to a class defined in a laser standard indicating a safety standard of a laser product to the laser light emitted from the first light source and then emitted from the light guide.

(9) The medical light source device according to any one of (1) to (8), wherein the laser light is excitation light that generates fluorescence from the subject with irradiation of the subject, and the measurement light is in a wavelength band different from wavelength bands of the excitation light and the fluorescence.

(10) A medical observation system including: a medical light source device configured to emit laser light; a light guide configured to guide the laser light; and an emission optical system configured to irradiate a subject with the laser light through the light guide, wherein the medical light source device includes: a first light source configured to emit the laser light; a second light source configured to emit measurement light for measuring a connection state between the light guide and the emission optical system to the light guide; and a control unit configured to control output of the laser light in the first light source based on return light of the measurement light emitted from the second light source.

The medical light source device and the medical observation system according to the present disclosure may secure the light amount of laser light emitted to a subject while securing safety.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical light source device comprising:

a first light source configured to emit laser light;

a second light source configured to emit measurement light for measuring a connection state between a light guide configured to guide the laser light and an emission optical system configured to irradiate a subject with the laser light through the light guide;

an optical measurement device configured to measure the connection state by using an optical time domain reflectometer (OTDR), the optical measurement device including the second light source and being configured to generate an OTDR waveform indicating a light amount level of the return light with respect to a distance from the medical light source device; and a control circuit configured to control output of the laser light in the first light source based on information indicating a peak in the OTDR waveform.

2. The medical light source device according to claim 1, wherein the control circuit is configured to determine whether there is a peak of the light amount level of the return light at a specific distance from the medical light source device based on the OTDR waveform, and control output of the laser light in the first light source based on a result of the determination.

3. The medical light source device according to claim 1, wherein the control circuit is configured to determine whether number of peaks in the OTDR waveform is a specific number, and control output of the laser light in the first light source based on a result of the determination.

4. The medical light source device according to claim 1, wherein the control circuit is configured to further control output of the laser light in the first light source based on information indicating a change in the light amount level of the return light within a range defined by a specific distance from the medical light source device in the OTDR waveform.

5. The medical light source device according to claim 1, wherein the control circuit is configured to cause, based on the return light, a notification device to notify warning information indicating a warning.

6. The medical light source device according to claim 1, wherein the second light source is configured to cause the measurement light to be emitted in pulses at a cycle less than a time reference corresponding to a class defined in a laser standard indicating a safety standard of a laser product to the laser light emitted from the first light source and then emitted from the light guide.

7. The medical light source device according to claim 1, wherein the laser light is excitation light that generates fluorescence from the subject with irradiation of the subject, and the measurement light is in a wavelength band different from wavelength bands of the excitation light and the fluorescence.

8. A medical observation system comprising:

a medical light source device configured to emit laser light;

a light guide configured to guide the laser light;

an optical measurement device configured to measure the connection state by using an optical time domain reflectometer (OTDR), the optical measurement device including the second light source and being configured to generate an OTDR waveform indicating a light amount level of the return light with respect to a distance from the medical light source device; and an emission optical system configured to irradiate a subject with the laser light through the light guide, wherein the medical light source device includes:

a first light source configured to emit the laser light;

a second light source configured to emit measurement light for measuring a connection state between the light guide and the emission optical system; and a control circuit configured to control output of the laser light in the first light source based on information indicating a peak in the OTDR waveform.

9. The medical light source device according to claim 1, wherein the control circuit is configured to determine whether the light guide and the emission optical system are appropriately connected based on information indicating the peak in the OTDR waveform generated from the return light.

10. The medical light source device according to claim 9, wherein the control circuit is configured to determine that the light guide and the emission optical system are not appropriately connected when a number of peaks in the OTDR waveform is not a specific number.

11. The medical light source device according to claim 10, wherein, in response to the light guide and the emission optical system not being appropriately connected, the control circuit is configured to stop an output of the laser light from the first light source that the light guide and the emission optical system are not appropriately connected, otherwise, continuing the output of the laser light from the first light source.

12. The medical light source device according to claim 10, wherein, in response to the light guide and the emission optical system not being appropriately connected, the control circuit is further configured to output warning information.

13. A method for controlling a medical light source device including a first light source for emitting laser light and a second light source, the method comprising:

emitting, from the second light source, measurement light for measuring a connection state between a light guide configured to guide the laser light and an emission optical system configured to irradiate a subject with the laser light;

measuring the connection state by using an optical time domain reflectometer (OTDR), the optical measurement device including the second light source and being configured to generate an OTDR waveform indicating a light amount level of the return light with respect to a distance from the medical light source device; and controlling output of the laser light in the first light source based on information indicating a peak in the OTDR waveform.

14. The method according to claim 13, comprising:

determining whether there is a peak of the light amount level of the return light at a specific distance from the medical light source device based on the OTDR waveform, and controlling output of the laser light in the first light source based on a result of the determination.

15. The method according to claim 13, further comprising:

determining whether number of peaks in the OTDR waveform is a specific number, and controlling output of the laser light in the first light source based on a result of the determination.

16. The method according to claim 15, further comprising, in response to the number of peaks in the OTDR waveform not being the specific number, stopping an output of the laser light from the first light source, otherwise continuing the output of the laser light from the first light source.

17. The method according to claim 15, further comprising, in response to the number of peaks in the OTDR waveform not being the specific number, outputting warning information.

18. The method according to claim 13, controlling output of the laser light in the first light source based on information indicating a change in the light amount level of the return light within a range defined by a specific distance from the medical light source device in the OTDR waveform.

19. The method according to claim 13, further comprising controlling the second light source to emit the measurement light in pulses at a cycle less than a time reference corresponding to a class defined in a laser standard indicating a safety standard of a laser product to the laser light emitted from the first light source and then emitted from the light guide.

20. The method according to claim 13, further comprising determining that the light guide and the emission optical system are not appropriately connected when a number of peaks in the OTDR waveform is not a specific number.

*   *   *   *   *